(12) United States Patent
Brem

(10) Patent No.: US 6,509,187 B2
(45) Date of Patent: *Jan. 21, 2003

(54) METHOD AND DEVICE FOR COLLECTION AND PREPARATION OF TISSUE SAMPLES FOR MOLECULAR GENETIC DIAGNOSTICS

(75) Inventor: Gottfried Brem, Larezhausen (DE)

(73) Assignee: Agrobiogen GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/423,187
(22) PCT Filed: May 25, 1998
(86) PCT No.: PCT/EP98/03075
§ 371 (c)(1), (2), (4) Date: Mar. 20, 2000
(87) PCT Pub. No.: WO99/61882
PCT Pub. Date: Dec. 2, 1999

(65) Prior Publication Data
US 2002/0137033 A1 Sep. 26, 2002

(51) Int. Cl.[7] .............................. C12M 1/34; C12N 1/08; B01D 11/02
(52) U.S. Cl. .................. 435/288.2; 435/183; 435/270; 422/243; 422/255; 422/261
(58) Field of Search .................. 435/6, 270, 287.2, 435/183, 288.2; 422/50, 61, 243, 255, 261; 40/301; 452/198

(56) References Cited

U.S. PATENT DOCUMENTS

| | | | |
|---|---|---|---|
| 3,731,414 A | * 5/1973 | Murphy et al. ............... | 40/301 |
| 4,230,001 A | 10/1980 | Noll et al. | |
| 5,126,276 A | 6/1992 | Fish et al. | |
| 5,396,898 A | 3/1995 | Bittmann et al. | |
| 5,461,805 A | * 10/1995 | Johnson ....................... | 40/301 |
| 5,741,177 A | 4/1998 | Roberts et al. | |
| 5,741,957 A | * 4/1998 | Deboer et al. .................. | 800/2 |
| 6,087,097 A | * 7/2000 | Persing .......................... | 435/6 |
| 6,095,915 A | * 8/2000 | Geissler et al. ............. | 452/198 |
| 6,153,428 A | * 11/2000 | Gustafsson et al. ......... | 435/325 |

FOREIGN PATENT DOCUMENTS

| | | |
|---|---|---|
| EP | 0 734 768 A1 | 3/1986 |
| GB | 2 137 340 A | 10/1984 |
| WO | WO 96/13214 | 5/1996 |

* cited by examiner

Primary Examiner—Bradley L. Sisson
(74) Attorney, Agent, or Firm—Bell, Boyd & Lloyd LLC

(57) ABSTRACT

The present invention refers to a device and a procedure for the collection and initial preparation of tissue/blood or other sample of nucleated or DNA-containing cells or cell components for molecular genetic investigation. The invented device for the collection and initial preparation of samples of DNA-containing cells includes a sample receiving container and means for the collection of the sample, which is introduced into the sample receiving container after collection of the sample and seals this tightly. The sample receiving container has a base and side walls, is closed with a easily penetrable lid and has—in an area of the side walls of the container removed from the base—means to secure the introduced sample collection tool; in the container are substances to protect from DNA-degrading enzymes. The tool for the collection of the sample is so formed that on introduction into the sample receiving container it is secured in place by the means in the sample receiving container for securing, and divides the sample receiving container into at least one sample space, which is limited by the base and the side walls of the sample receiving container and the front end of the sample collection tool.

17 Claims, 4 Drawing Sheets

METHOD AND DEVICE FOR COLLECTION AND PREPARATION OF TISSUE SAMPLES FOR MOLECULAR GENETIC DIAGNOSTICS

BACKGROUND OF THE INVENTION

1. Field of the Invention

This invention relates to a device and a method for collecting and initially preparing tissue, blood or other samples of nucleated or DNA-containing cells or cell components for molecular genetic testing. The invention also relates to the use of the device described here for the typing of animal populations.

2. Description of the Background

The collection of a large number of tissue- or DNA-samples is necessary for diverse research and applied programs. Under certain circumstances information about entire farm animal populations (e.g. biologically dynamic animal production) or regionally or specially characterized animal populations must be collected.

In this way, for example, triggered by the BSE scandal and the associated problems of ensuring that meat and products originate from unaffected farms, EU-wide compulsory identification of farm animals was introduced, in which—at or shortly after birth—animals are provided with ear tags for their identification. These have an individual number which identifies each farm animal. Thus, by checking the number, it is for example possible to determine at a later date, in the abattoir, which farm the animal comes from.

However these ear tags are not safe from forgery and can be exchanged by manipulation, so that the identification system introduced can be evaded. The consumer or the middle man cannot ensure if the animal really comes from the farm stated.

It would therefore be desirable to have a simple analytical method available which provides for the independent confirmation of the information from the producers, processors and marketers.

As is well known, each animal can be individually identified by testing certain DNA variants ("genetic fingerprint"). In forensic science and in the parentage testing of breeding animals these innovative molecular genetic tests are already being used for analysis; the sample from the animal is usually collected as a blood sample by the veterinarian and analyzed. However, for larger animal populations this is too labor-intensive and not practicable from an economic point of view.

With the help of modern detection methods (PCR, sequencing, etc) it can be determined, even from very small tissue samples, whether or not they derive from a particular individual. The test can be carried out relatively easily, with a reliability of over 99.9%.

However, at present the expense in terms of finance and labor to carry out separate, targeted collection, preservation, cataloguing, and analysis of such numbers of samples is enormous.

SUMMARY OF THE INVENTION

The present invention relates to a device with which collection of DNA-containing samples from subjects can be carried out easily and cost-effectively.

This invention relates to a method with which tissue or blood samples can easily be collected from subjects for analytic investigation.

This invention also relates to a device for the easy and cost-effective collection of DNA-containing samples from subjects. The present device for the collection and initial preparation of samples of DNA-containing cells comprises a sample receiving container and a tool for collecting the sample. After collecting the sample, the sample collection tool is introduced into the sample receiving container and tightly seals it. The sample receiving container has a base and side walls and is closed with an easily penetrable lid. In an area of the side walls away from the, base are means to secure the introduced sample collecting tool, and substances placed in the container protect against DNA-degrading enzymes. The tool to collect the samples is formed in such a way that on introduction into the sample receiving container, the means to secure this tool (provided in the sample receiving container) fastens, it securely in place and the tool divides the sample receiving container into at least one sample space limited by the base and side walls of the sample receiving container and the front end of the sample collecting tool.

The device of the present invention may be applied to collecting a suitable sample the sample collecting tool and, introduce it into the sample receiving container, so that through the base and the side walls of the sample receiving container and the front part of the sample collecting tool a limited sample space is formed, which is closed to the environment.

The invention will now be explained with the help of the accompanying diagrams.

Figure 1:
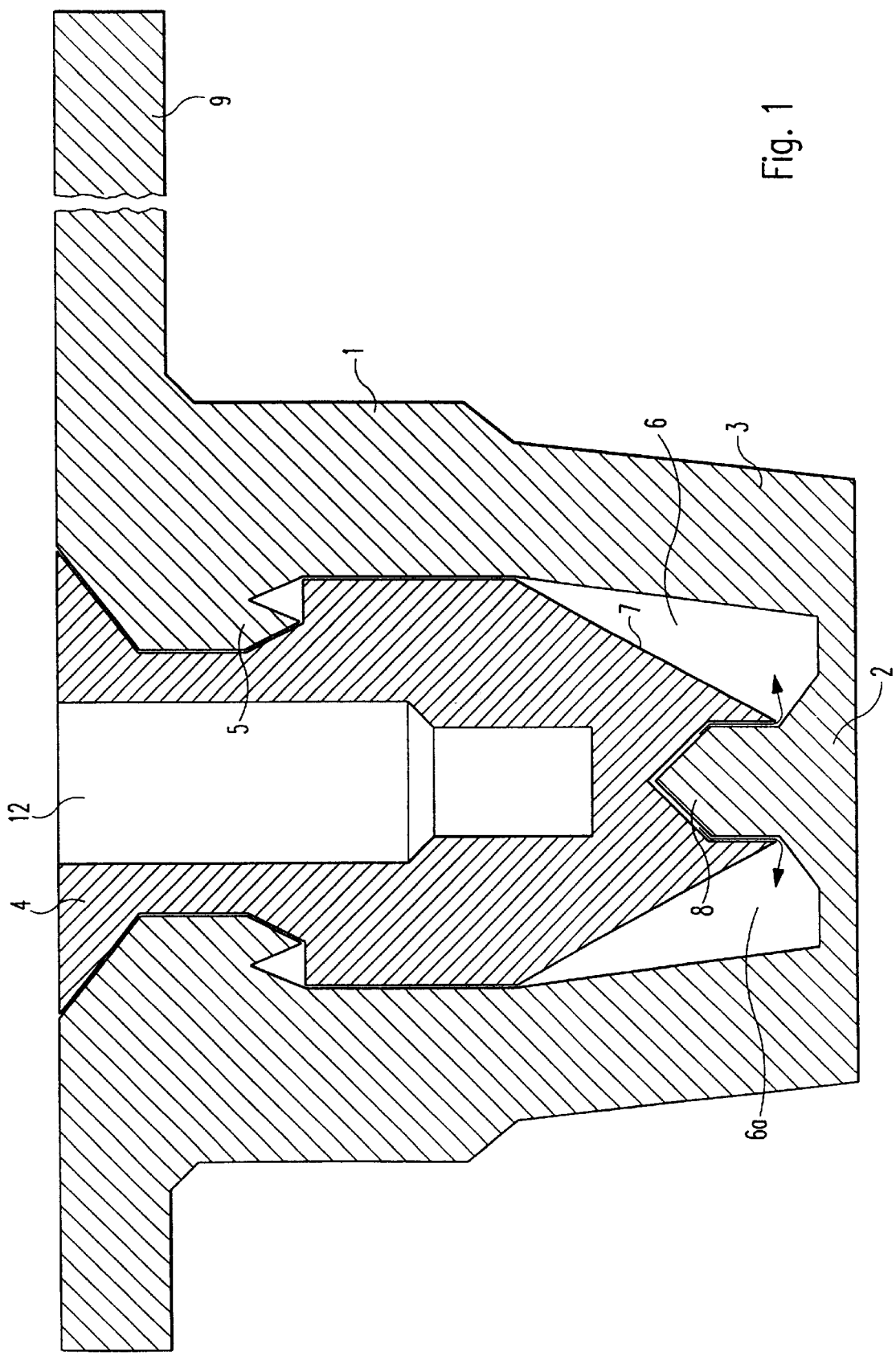
FIG. 1 shows a cross-section of a model of the sample receiving container 1, which has a projection 8 on its base 2. The sample collection tool 4 is in the sample receiving container 1, and tightly seals this. On the side of the sample collection tool 4, away from the sample space 6,6a is a hollow 12 to allow for the insertion of a rod.
Figure 2:
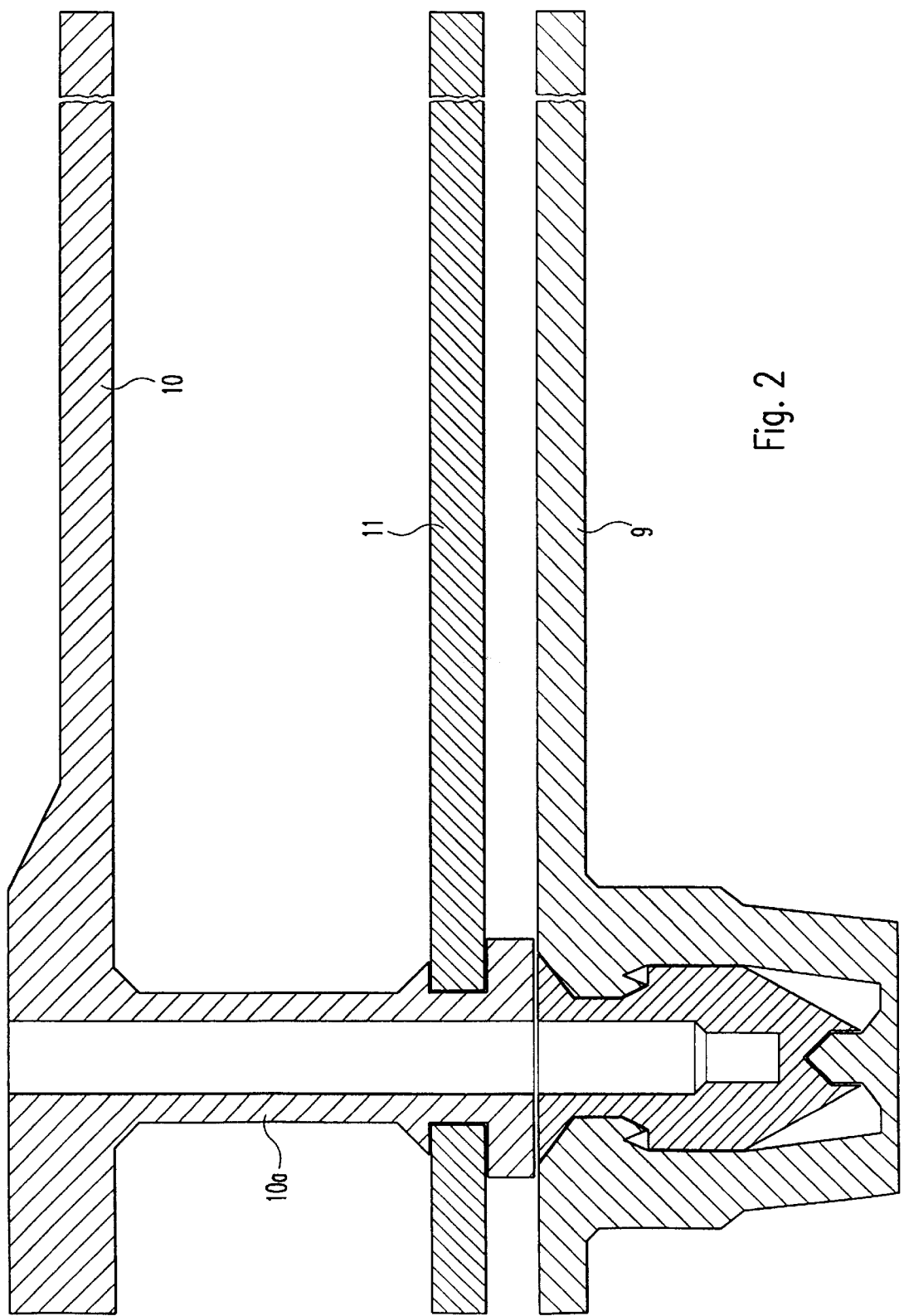
FIG. 2 shows a cross-section of an arrangement of spike plate 10 with spike 10a, aperture plate 11 with sample receiving container 1 with attached tongue 9. The sample receiving container 1 is closed with the sample collection tool 4, depicting the situation after application of an ear tag 10,11 and simultaneous collection of a sample.

DESCRIPTION OF THE PREFERRED EMBODIMENTS OF THE INVENTION WITH REFERENCE TO THE DRAWINGS

The invention will now be described in more detail using the preferred model and with reference to the figures.

The invented device contains a sample receiving container 1 and sample collection tool 2.

The sample receiving container 1 has a base 2 and side walls 3, and is closed with an easily penetrable lid such as a film or membrane. The sample receiving container 1 can itself be subdivided by additional membranes, so that two or more components can be separated from each other in the sample receiving container 1 until use, and only on entry of the sample collection tool 4 into the container 1 come into contact with each other and with the sample. The sample receiving container 1 can furthermore be subdivided by a separating wall, such as a projection 8 stretching over the whole diameter of the base 2, into at least two chambers, so that on sample collection at least two completely separate samples can be collected.

In a preferred model the sample receiving container 1 receives at least the front end of the sample collection tool 4. If necessary it s base 2 can be formed so that it has a tapered projection 8; the sample collection tool 4 appropriately fits together with the projection 8. As a result, on entry of the sample collection tool 4 into the sample receiving container 1 the sample is strongly crushed and pressed into the sample space 6, 6a limited by the base 2 and the side walls 3 of the sample receiving container 1 as well as the front part 7 of the sample collection tool 4.

The sample receiving container 1 can also possess a holding device 9 such as a flat attachment, for example a tongue with a hole to fasten this appropriately. Thus, for example, the tongue can be fastened to the pliers when pliers are being used to apply the ear tag 10,11. The tongue is also suitable for taking the identification number, which is the same as that of the ear tag. Labeling can take place by hand in the grooves provided, or the tongue can be pre-labeled e.g. imprinted, or can be printed at the same time and identical to the identification number applied onto the plate part of the ear tag 10,11.

If necessary (e.g. for further processing of the samples by hand) the sample receiving container 1 can also be so formed that the area of the sample receiving container 1 which defines the sample space 6, 6a after closure with the sample collection tool 4, is connected by a screw thread to the body of the sample receiving container 1 and thus can easily be unscrewed, enabling easier as to the sample.

In a preferred model of the device the sample receiving container 1 is closed by the sample collection tool 4 in such a way that opening the sample space 6,6a formed is not possible without destroying the device. Thus it is certain that manipulation of the collected sample is not possible without it being noticed.

In the sample receiving container 1 are substances to inactivate the protein component of the tissue sample and stabilize the DNA.

The substances to inactivate the proteins (enzymes, DNAses, etc.) of the tissue sample and to stabilize the DNA can for example be selected from the group consisting of:

Proteinase K (e.g. lyophilized for stabilization during storage) and (separately filled) buffer to digest proteins; Strong bases; Molecular sieve (e.g. E. Merck 0.2 nm No. 1.05704.0250, K 230045904 624, water absorption capacity >20%), which is extremely hygroscopic and dries out the tissue sample on contact with it (and warms it) and thereby inactivates. To protect the molecular sieve from undesired uptake of moisture from the air it can, for example, be coated with the inert gas argon and closed with a film. Other components, which support the inactivation of the protein component and the stabilization of the DNA. The substances are so formulated that they remain active for a long period of time, for example up to one year or longer, and after introduction of the sample ensure sufficient integrity of the DNA for analytic investigation for at least many months up to one year.

The sample collection tool 4 can take any form with which the sample can be collected and introduced into the sample receiving container 1, in which the sample collection tool 4 seals closed the sample receiving container 1 after introduction. This includes the form of cylinders, cones, etc.

In a preferred model of the. device the sample collection tool 4 consists of two parts, which before use are connected (but separable) to each other and with use separate from each other. This can for example be realized by a narrow bridge of plastic with a specified breaking point. The sample collection tool 4 can be solid or can at its rear side allow for the insertion of a rod, for example with a central hollow 12, into which a steel rod from pliers can be introduced for stabilization on use.

The sample collection tool 4 carries out several functions. The sample is collected with it, for example by simply immersing it in body fluids such as blood, lymph or urine or by scratching or punching out tissue from the subject.

With a preferred model, the ear of the subject is pierced with the invented device; the front end of the sample collection tool 4 can be formed with a sharp edge so that by pushing through the ear a small tissue sample is punched/ crushed out.

In a further preferred model of the device the sample collection tool is provided with a suitable instrument, such as ear tagging pliers, that is applied at the same time as an ear tag is pressed through the ear of a subject. In this manner, the application of the ear tag and the collection of the sample take place in one working procedure.

The ear tags used for identification usually consist of two parts, a plate carrying a spike 10 (spike plate) and an aperture plate 11, which has about the same size as the spike plate 10 or can consist of a smaller plate, which only has to be large enough to prevent the spike 10a from sliding out to the ear. Both parts are made from tissue compatible synthetic material suitable for use with food (e.g. polyurethane— Desmopan 795® from Bayer) or in part from metal (e.g. stainless steel, brass, bronze or such like).

To insert the ear tag 10,11 commercial ear tagging pliers can be used. Most of the pliers available for this purpose can if necessary very easily be modified by the addition of a small extra part, so that the sample receiving container 1 remains hanging on the pliers after insertion of the ear tag 10,11 and can therefore easily be collected. The extra part is for example a small knob over which the hole in the tongue 9 with the sample receiving container 1 is drawn. After insertion of the ear tag 10,11 in the ear, if necessary the ear tag 10,11 is abruptly withdrawn from the hold in the pliers and the knob holds the tongue 9 with the sample receiving container 1 firmly on the pliers. Subsequently the tongue can easily be drawn over the knob and thus the sample receiving container 1 can be collected.

The sample collection tool 4 tightly closes the sample receiving container 1 on introduction, and is fixed in place by fixation means 5, so that escape of sample material and entry of foreign material is prevented.

The sample receiving container 1 as well as the sample collection tool 4 can be made from any suitable material, such as for example metal or from glass-fiber reinforced synthetic material. If the sample collection tool 4 is made from synthetic material it can be reinforced during insertion in the ear by a metal rod in the pliers used.

With the invented device it is possible to take samples from animals at the same time as the identification marking with ear tags 10,11 which is routinely performed, without much additional effort or expense. The savings resulting from this are very substantial.

A further advantage of the invented device compared with conventional sample receiving containers is the holding device 9 on the sample receiving container, which has the form of a flat tongue and can be used label/identify the sample. Usually labeling has to take place by hand on the mostly round surface of the mostly cylindrical containers (e.g. Eppendorf tubes) with considerable effort and results which can be hard to read. It is therefore difficult to scan in numbers or data and automate collection.

The invented system is of particular advantage when samples have to be taken from material which is still part of a whole structure, so that a sample would normally have to be taken with an instrument (knife, sharp spoon, scalpel etc). With the use of reusable instruments the danger of contamination is very high, as with very sensitive tests such as PCR (polymerase chain reaction) even single cells can lead to contamination and thereby to false positive results. With the use of the invented device only single use parts come into contact with the sample material.

The invented device can also, for example, be used to reliably and securely collect and process fluid samples (blood, urine, saliva and others). In this case the fluid is applied to either the opening of the sample receiving container 1 or onto the front part of the sample collection tool 4 and subsequently, for example with a suitable device such as pliers, pressed into the sample receiving container 1. Samples from surfaces (skin, mucous membranes etc.) can also be collected, cleanly, reliably and with secure identification using the invented device in that the front part of the sample collection tool 4 is used as a "sharp spoon" and briefly drawn/scraped over the surface.

A substantial advantage of the invention is that the sample receiving container 1 can be labeled at the same time as the ear tags (spike plate 10, aperture plate 11)—thereby unmistakably having the same numbering n̄ before distribution to the users or owners of the animals. The labeling can, for example, be carried out with a printer, with which in the case of plastic ear tags a (black) mastermix is applied which binds so strongly with the synthetic material that it cannot be wiped off or removed with normal use. Furthermore, the corresponding parts can have an individual number printed onto them.

The samples collected with the invented device are then brought to a central collecting location and analyzed there. The collection of the sample receiving container 1 can take place without special consideration to temperature and duration of transport. The sample receiving containers 1 can be transported by post, courier, or sample collection to the laboratory or to be placed into storage, problem free and risk-free.

The work up of the samples in the laboratory n̄ taking an aliquot, test reactions and analysis n̄ can be automated with a robot controlled system. The identification number of the samples is registered and further processed by a reading device (scanner). By avoiding the entry of data by hand the number of mistakes can be kept negligibly low.

To process or analyze the DNA from the samples collected with the invented devices, the sample receiving containers 1 are put onto a conveyor belt so that a scanner can record the identity of the sample. Subsequently a canula is inserted through the floor of the sample space 6,6a and fluid is injected for the uptake of the sample and then an aliquot is taken. The point of insertion can then be sealed again so that the sample receiving container can be stored. If the sample space 6,6a was divided in a suitable way to begin with, then there are further samples available for analysis in the invented device.

DNA isolation can be automated through the use of a pipetting robot (Biomec2000®, Beckman) and the DNA purification using silicon particles (e.g. InstaGene Matrix, BIO-RAD). Test reactions with these samples can also be prepared by automation.

The system described here for the easy collection of samples and automated analysis has the following advantages.

Forgery-free proof of origin and identity for all cattle and meat from these cattle, in all stages of processing up to consumption and thereby proof of origin from BSE free areas. Enables control and with this stabilization of targeted sales programs such as animals kept on organic farms or kept on national parks or with special grade identification. Verification and monitoring of the transport routes and times and distances for all cattle transport. Efficient border control and follow up of cattle within the EU and on international export. Unmistakable identification of all breeding cattle sold with confirmation of identity possible at any time e.g. at auctions, exhibitions etc. Complete proof of origin for all cattle born and detection of mistaken or falsified papers. Completely reliable forensic evidence (also from already consumed beef from the stomach contents by the medical examiner). Completely reliable monitoring of (culling) and epidemic control. Determination of the mix of beef in all (processed) foodstuffs tested, including in pet food. Detection of producers from abattoirs where in the course of random testing treatment with banned hormones or growth promoters have been carried out. Proof of origin for other products from cattle production such as hides, bones, horns, hooves, organ preparations, blood etc. Proof and testing of the animal and stock origin with directly sold milk and milk products. Exact registration of all cattle herds and routes of sale. Samples for detailed analysis of DNA polymorphisms, measurements of genetic distance and genetic screening programs would be available.

Optimization of breeding programs. Measurement of genetic distance. Investigation of genealogical and breeding history of animal breeds. Analyses as part of marker assisted selection programs (MAS). Exact evidence of the presence and frequency of particular genetic defects. From a forensic point of view the device and the procedure of the present invention have the further advantage that the collected sample cannot be changed (exchanged, falsified) without the necessary manipulation of the sample receiving container being recognizable.

The hygiene of food processing operations may be monitored without great expense by collecting and cataloguing the samples, typing them, conducting testing of origin, screening of genetic defects, population analyses, mutation detection, screening of food-stuffs, pathogen diagnosis, and transgenic diagnosis.

The system described here permits testing and screening the genetic information present in all animals (animal samples) and in all products of animal origin prior to their consumption. The utilization of the present device reduces the costs normally associated with these procedures several fold.

Figure 3:
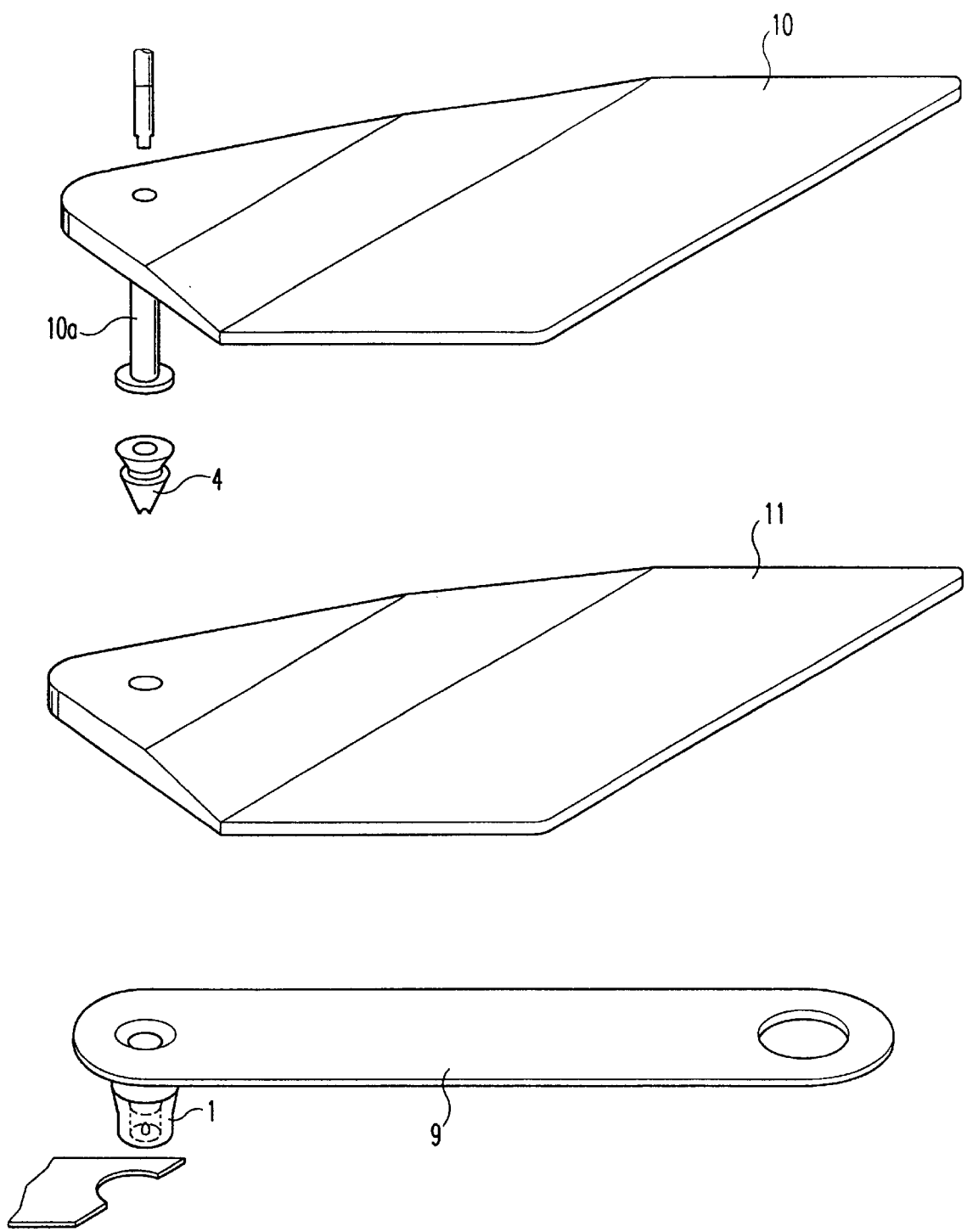
FIG. 3 shows a side view of an ear tag 10,11 consisting of spike plate 10 and aperture plate 11, and a sample receiving container 1 complete with tongue 9, before being put together using a suitable device.

The present technology permits the identification of individual specific DNA and its species of origin even in intensively processed food of animal origin, such as sausages, processed meat, "Leberkäs" (finely ground meat with spices and other ingredients, to be baked in the oven or available ready-baked), schnitzel or the like. It is thereby possible to detect contamination of food with foreign meat components. Of course it is also possible with the help of this method to prove beyond doubt that a particular foodstuff derives from a particular animal—as stated—if on the original farm a suitable (first) sample was taken (FIG. 3).

For this an ear tissue sample must be taken from every new-born farm animal for DNA typing and transported to the typing center. There using (automated) PCR DNA fingerprints from microsatellite primers are made and an unmistakable pattern for each animal is registered.

Figure 4:
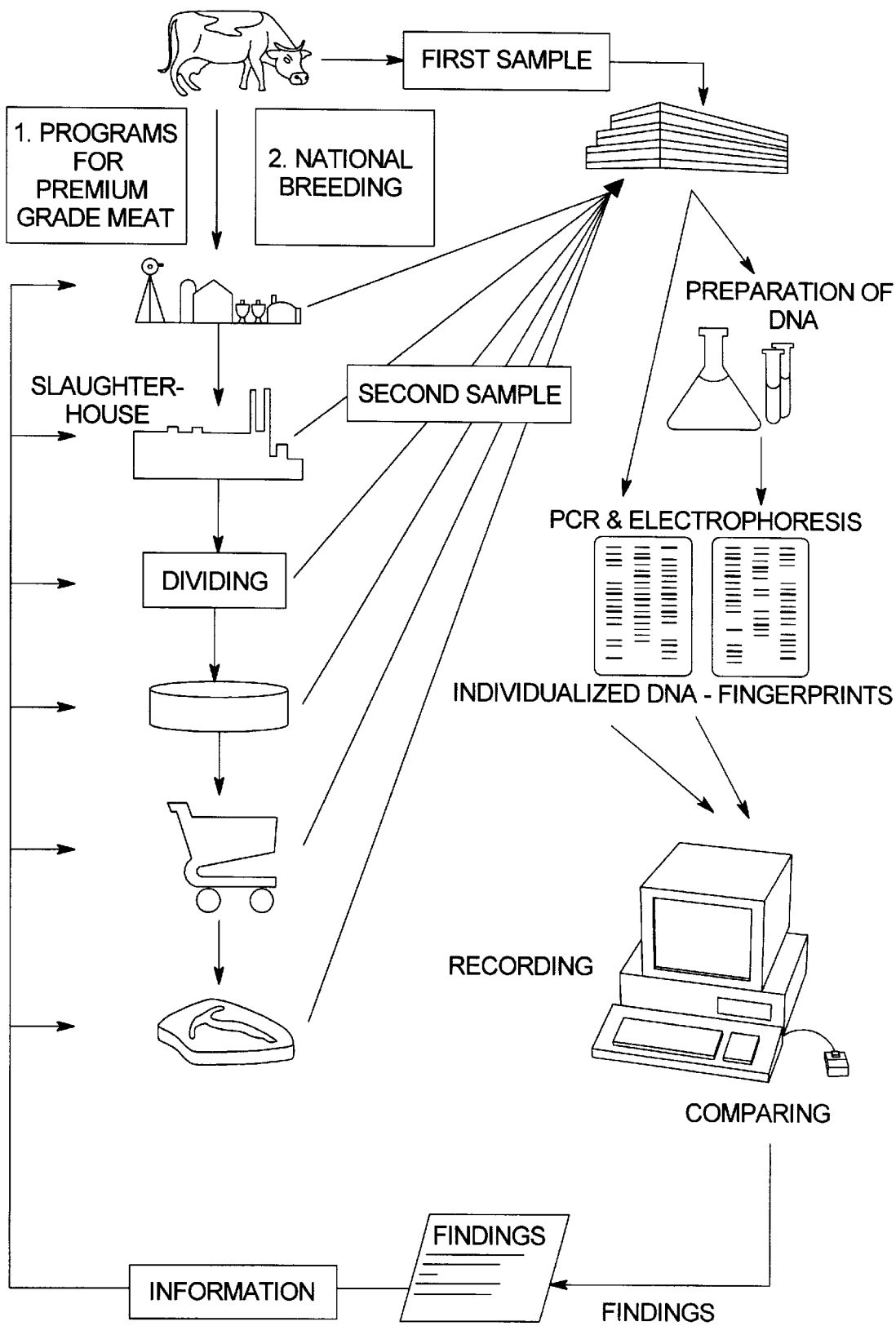
FIG. 4 shows a diagram of individual DNA typing in cattle.

These data are saved in a central file and made accessible throughout. A fingerprint for an unknown sample may be obtained in a routine test, and thereby fingerprints in earlier analyses of the matching animal source can be found. This result is normally available within one day. In extreme cases, e.g., in the transport of animals or border control, results can be available within three hours. The identification of the animal, i.e., the DNA fingerprint and all other data, can be called up for every animal registered. The owner of the animal, i.e., all animals sold by one owner or from one herd, can be pooled. After several years of registration of all cattle born, the parentage (i.e., the parents of the animal) and the number of offspring of each parent can be looked up via this file. Individually typing of a complete population of farm animals is, in accordance with this invention, uniquely discovered. Every consumer, guest, customer, dealer, butcher, processor, owner or inspector can check on the identity, and thereby the origin, of an animal or animal product as illustrated in FIG. 4. For this test, it is merely necessary to take a second sample, such as from the abattoir (slaughter house), the supermarket or even the already prepared meal, for example, in a restaurant from a schnitzel (a piece) already on the table.

With live animals e.g. in checking that animals have been transported in an approved manner (distance) typing would similarly be possible. This degree of certainty for the test results will, with a sufficiently high testing frequency, automatically lead to fraud being reduced to a minimum due to fear of reliable and legally incontestable evidence and risk of detection.

All orders which may be made in the future to monitor particular groups of animals or herds for reasons of risk prevention, epidemic control or testing for illegal residues (hormones, growth promoters etc.) in animals, could be immediately undertaken using the DNA data already collected.

If individual typing with the system described here is consistently carried out in a country, one will at all times be in the position to immediately, i.e. on the same day, react to problems which arise (e.g. suspicion of BSE in an animal, outbreak of swine fever on a farm etc.) thereby providing for the consumer unparalleled protection and unparalleled testing possibilities for monitoring.

In particular it would be possible, for example, through individual typing to completely and beyond doubt prove that animals and products from "alternative" production really derive from there. That means that every customer could arrange testing of the information accompanying the meat, even after lengthy transport and sale of the meat, by sending in samples (second sample).

The invention will now be explained in more detail using examples, which are not to limit the invention described in the claims.

EXAMPLE 1

Individual Typing in Cattle

A cow has been marked with a conventional ear tag. On the spike of the spike plate the sample collection tool was attached, which has the form of a cone with the point at the front and a cylindrical base and a cavity in the base for accepting the spike of the spike plate.

On the pliers the sample receiving container, made in one piece with the tongue, was positioned under the position provided for the aperture plate in such a way that the lid of the sample receiving container ñ closed with a lid of synthetic film ñ was lined up with the hole of the aperture plate.

In a location away from the sample receiving container the tongue had a hole for securing it in place on the pliers.

By pressing the spike provided with the sample collection tool of the spike plate, through the ear of the cow, the sample of the ear punched out was pressed into the sample receiving container. After entry the sample collection tool was fixed in place by the projections on the inside walls of the sample receiving container, whereby the sample space formed was sealed closed.

In the sample receiving container was a molecular sieve (Merck, 0.2 nm Nr. 1.05704.0250), which protects the DNA of the collected sample from degradation.

DNA footprints and PCR analyses of known genes could be undertaken problem free on the genetic material present in the sample receiving container after half a year.

EXAMPLE 2

Screen-out of functional mutants for the breeding of special lines (e.g. of 1.3Gal/Gal3 negative pigs for xenotransplantation).

Due to the natural mutation rate, in a population of sufficient size in single individuals every gene present in the genome contains not just various silent mutations, but rather with a certain probability also mutations which result in an inactivation of the allele. In the majority of these cases this involves recessive rather than dominant mutations. According to the Hardy-Weinberg law the predominant number of such changes in genotype caused by mutations is masked by heterozygote individuals.

In a screening procedure it is critical to discover using suitable molecular genetic analyses of the appropriate locus in the available pig population, a (single) heterozygous carrier animal which has the mutation. Then a homozygous negative line can be built up with this animal, which has the same desired and needed gene defect as a line generated through gene knockout. It would in no way be inferior to this.

The suggested approach represents to a certain degree the screening of a stem cell line after recombination with a suitable construct which contains no marker. The difference is the following: all cells of a stem cell line have the same genotype with the exception of those, which have a change or recombination after the single mutation event. In the screening of pig populations all the analyzed genotypes are different. They have not be mutagenized in a targeted way but carry mutations, which in the course of evolution and work of breeders have accumulated (as long as in the heterozygote state they were under no negative selection pressure).

It is known that there are quantitative differences in the expression of 1.3Gal/Gal3. As the mutation analysis is aimed at finding already present mutations in diverse populations, breeding animals will be analyzed. If one ignores new mutations, then production pigs can only carry mutations which were already present in the breeding parents. For practical completion the preservation and collection of tissue samples with the Typi-fix system is a critical factor for success or financial realization. In the analysis to find mutation carriers it must be assumed that possibly up to 100,000 genotypes will have to be tested in order to find potential animals with a 1.3Gal/Gal3 deficiency. For the costly collection of individual samples from 100,000 pigs the invented system is the method of choice. The samples need only to be transported into the laboratory (by mail or sample collection) and further worked up there.

What is claimed is:

1. An apparatus for the collection and initial preparation of samples of DNA-containing cells, the apparatus comprising:

a sample-receiving container comprising a base and side walls, a penetrable lid for closing the container, and a sample-collection-tool-securing means formed on the side walls of the sample-receiving container in an area removed from the base;

a sainple-collection tool for collecting a sample, the sample-collection tool comprising a first end adapted to receive the sample and be placed in the sample-receiving container wherein the sample-collection tool is adapted to fit the sample-receiving container in sealing engagement upon penetration of the penetrable lid; and means for protecting the sample from DNA-degrading enzymes comprising a proteinase K and a suitable buffer, the means for protecting the sample is provided in the sample-receiving container, wherein upon entry of the sample-collection tool into the sample-receiving container, the sample-collection tool becomes affixed in place by the sample collection-tool-securing means thereby defining a sample space within the sample-receiving container wherein the sample space is delimited by the base and the side walls of the sample-receiving container and the first end of the sample-collection tool, and wherein the apparatus further comprises a membrane that separates the proteinase K from the suitable buffer, wherein the membrane is penetrated upon entry of the sample-collection tool into the sample-receiving container allowing the proteinase K to contact the buffer.

2. An apparatus for the collection and initial preparation of samples of DNA-containing cells, the apparatus comprising:

a sample-receiving container comprising a base and side walls and a penetrable lid for closing the container;

a sample-collection tool for collecting a sample comprising a first end adapted to receive the sample and be placed in the sample-receiving container, wherein the tool is adapted to fit the sample-receiving container in sealing engagement upon penetration of the penetrable lid;

means for securing the sample-collection tool within the sample-receiving container wherein the means for securing is formed on the side walls of the sample-receiving container in an area removed from the base; and means for protecting the sample from DNA-degrading enzymes, the means for protecting the sample being located in the sample-receiving container, wherein upon entry of the sample-collection tool into the sample-receiving container, the sample-collection tool becomes affixed in place by the means for securing the sample-collection tool thereby defining a sample space within the sample-receiving container, the sample space is delimited by the base and the side walls of the sample-receiving container and the first end of tbe sample-collection tool, wherein the base of the sample-receiving container further includes a projection into an internal space of the sample-receiving container, and the first end of the sample- collection tool is adapted to accept the projection so that when the sample is introduced into the sample-receiving container by the sample collection tool, the sample is crushed between the projection and the sample-collection tool.

3. The device of claim 2, wherein the projection is connected with the side walls of the sample receiving container in a manner such that upon introduction of the sample collection tool the sample receiving container is divided into two sample spaces.

4. The device of claim 2, wherein the projection is provided with a conical form.

5. The device of claim 2, wherein the projection is a wall dividing the sample receiving container into two areas.

6. An apparatus for collecting and initially preparing samples comprising DNA containing cells from an animal, the apparatus comprising:

a sample-receiving container including a base and side walls, a penetrable lid for closing the sample-receiving container, a sample-collecting-securing means formed on the sides walls of the sample-receiving container in an area removed from the base, wherein means to protect the sample from DNA-degrading enzymes is provided in the sample-receiving container; and a sample-collecting means comprising a first end adapted to receive the sample and be placed into the sample-receiving container wherein the sample-collection means is adapted to fit the sample-receiving container in sealing engagement upon penetration of the penetrable lid, wherein once the sample is collected and introduced into the sample-receiving container, the sample-collecting means can be fixed in place by the sample-collecting-securing means thereby defining a sample space within the sample-receiving container, wherein the sample space is delimited by the base and the side walls of the sample-receiving container and a first end of the sample-collecting means; and an ear tag including an aperture plate, a spike plate and means of verifying identity of the axial, wherein the sample-receiving container is releasably connected to the aperture plate of the ear tag and is provided with the same means of verifying identity as the ear tag, and wherein the sample-collecting means is releasably connected to the spike plate of the ear tag.

7. The apparatus according to claim 6, wherein the sample-collecting means is placed on a spike of the spike plate.

8. The apparatus according to claim 6, wherein the ear tag is enumerated.

9. The apparatus according to claim 6, wherein the sample-collecting means has at least one pointed edge at a first end of the sample-collecting means facing the base of the sample-receiving container.

10. The apparatus according to claim 9, wherein the first end of the sample-collecting means is tapered.

11. The apparatus according to claim 6, wherein the base of the sample-receiving container has a projection into an internal space and the first end of the sample-collecting means is adapted to accept the projection allowing the sample to be crushed between the projection and the sample-collection means.

12. The apparatus according to claim 11, wherein the projection comprises a cone form.

13. The apparatus according to claim 11, wherein the sample-receiving container is attached to a holding device.

14. The apparatus according to claim 13, wherein the holding device is a tongue.

15. The apparatus according to claim 6, wherein the sample-collecting means includes a second end opposite the first end, the second end includes an opening partially extending through the sample-collecting means thereby defining a cavity allowing insertion of a rod into the sample-collecting means.

16. The apparatus according to claim 6, wherein the means protecting the sample from DNA degrading enzymes is selected from the group consisting of an alkali, a proteinase K and a molecular sieve.

17. The apparatus according to claim 16, wherein the proteinase K is separated from a buffer by a membrane, which is penetrated on entry of the sample-collecting means, such that the proteinase K is brought into contact with the buffer.

* * * * *